United States Patent [19]

Pesson

[11] 4,129,737

[45] Dec. 12, 1978

[54] PROCESS FOR THE PREPARATION OF AN 8-ALKYL-5-OXO-5,8-DIHYDRO-PYRIDO(2,3-D)PYRIMIDINE-6-CARBOXYLIC ACID

[75] Inventor: Marcel Pesson, Paris, France

[73] Assignee: Laboratoire Roger Bellon, Neuilly-sur-Siene, France

[21] Appl. No.: 715,191

[22] Filed: Aug. 17, 1976

Related U.S. Application Data

[62] Division of Ser. No. 625,779, Oct. 24, 1975, which is a division of Ser. No. 384,203, Jul. 31, 1973, Pat. No. 3,950,338.

[30] Foreign Application Priority Data

Aug. 2, 1972 [FR] France ............................ 72.27876

[51] Int. Cl.$^2$ .......................................... C07D 471/04
[52] U.S. Cl. .................................... 544/279; 544/295; 544/117
[58] Field of Search ............... 260/256.4 F, 256.5 R, 260/287 AN

[56] References Cited

U.S. PATENT DOCUMENTS

| 3,397,208 | 8/1968 | Berman et al. ............... 260/287 AN |
|---|---|---|
| 3,641,028 | 2/1972 | Kim et al. ..................... 260/256.4 F |
| 3,673,184 | 6/1972 | Minami et al. ................ 260/256.4 F |
| 3,770,742 | 11/1973 | Matsumoto et al. .......... 260/256.4 F |
| 3,830,817 | 8/1974 | Narayanan ................... 260/287 AN |
| 3,843,645 | 10/1974 | Santilli et al. ................ 260/256.4 F |
| 3,849,421 | 11/1974 | Nakagome et al. .......... 260/287 AN |
| 3,887,557 | 6/1975 | Minami et al. ................ 260/256.4 F |
| 3,950,338 | 4/1976 | Pesson ........................... 260/256.4 F |
| 3,992,380 | 11/1976 | Lesher et al. ................. 260/256.4 F |

OTHER PUBLICATIONS

Morrison, et al, *Organic Chemistry*, 2nd ed., 1966, Allyn and Bacon, Inc., Boston, pp. 157–161, 483–491, 1084–1085.

Santilli, et al., "Journ. Hetero. Chem.-Anil", vol. 12, 1975, pp. 311–316.

Kiin, et al., "Tetrahedron Letters", 1971, No. 26, pp. 2441–2442.

Pesson et al., "Comptes Rendus", No. 10, 1974, pp. 714–719.

*Primary Examiner*—Jose Tovar
*Assistant Examiner*—James H. Turnipseed

[57] ABSTRACT

Valuable antibacterial 8-alkyl-5-oxo-5,8-dihydropyrido(2,3-d)pyrimidine-6-carboxylic acids, some of which are new compounds, are made from corresponding pyrimidines by a process involving condensation with an amino-ester, cyclization, halogenation, dehydrohalogenation, and saponification.

3 Claims, No Drawings

PROCESS FOR THE PREPARATION OF AN 8-ALKYL-5-OXO-5,8-DIHYDRO-PYRIDO(2,3-D)PYRIMIDINE-6-CARBOXYLIC ACID

This is a division of application Ser. No. 625,779, filed Oct. 24, 1975, which in turn is a divisional of Ser. No. 384,203 filed July 31, 1973 now U.S. Pat. No. 3,950,338.

The present invention provides a new process for the preparation of 8-alkyl-5-oxo-5,8-dihydropyrido(2,3-d)pyrimidine-6-carboxylic acids of the formula:

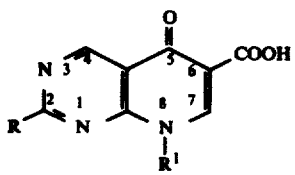

in which R is hydrogen, lower alkyl, lower alkoxy, lower alkylmercapto, phenyl, substituted phenyl, or a radical of formula —$NR_1R_2$ wherein $R_1$ and $R_2$, taken separately, each represent lower alkyl or, taken together, are bonded to one another to form with the nitrogen atom to which they are attached, a heterocyclic nucleus with 5 or 6 ring atoms which is unsubstituted or substituted and which can contain another heteroatom, such as pyrrolidino, piperidino, 4-hydroxypiperidino, morpholino, piperazino or $N_4$-substituted piperazino, and R' is lower alkyl. Preferred N-substituted piperazino radicals are those of the formula:

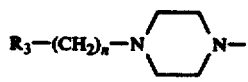

wherein n is 0, 1, 2, or 3, and $R_3$ is hydrogen, hydroxyl, vinyl, phenyl, or phenyl substituted by halogen or lower alkoxy. The term "lower alkyl" as used herein means an alkyl radical with 1 to 5 carbon atoms.

The compounds of formula I are valuable antibacterial agents, especially those in which R is 4-hydroxypiperidino, piperazino, or N-substituted piperazino, which are new compounds.

The process of the invention for the production of the aforesaid compounds comprises:

(a) condensing a 4-chloro-5-carbethoxy-pyrimidine of formula:

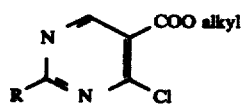

with a lower alkyl β-amino-propionate of formula:

to form a 4-N-(β-carbalkoxyethylamino)-5-carbethoxypyrimidine of formula:

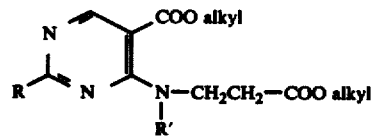

(b) cyclising the compound of formula III to form a 5-oxo-6-carbalkoxy-5,6,7,8-tetrahydro-pyrido(2,3-d)-pyrimidine of formula:

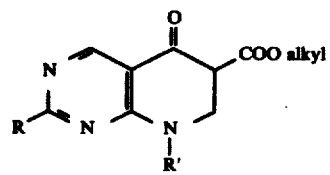

(c) halogenating the β-keto-ester of formula IV to yield the corresponding 6-halogeno derivative, (d) treating the said derivative with a base to bring about dehydrohalogenation to give a 6-carbalkoxy-5-oxo-5,8-dihydro-pyrido(2,3-d)pyrimidine of formula:

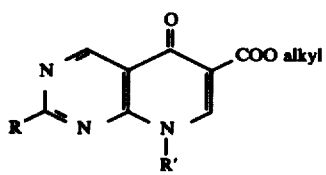

(e) and saponifying the compound of formula VI to yield the desired acid of formula I.

The starting material in this process is a 4-chloro-5-carbethoxy-pyrimidine (II), condensation of which with a lower alkyl (especially ethyl) β-aminopropionate, substituted at the nitrogen by the radical R', leads to a 4-N-(β-carbalkoxyethylamino)-5-carbethoxypyrimidine (III). Cyclisation of the latter, under the effect of a (preferably tertiary) alkali metal alcoholate forms a 5-oxo-6-carbalkoxy-5,6,7,8-tetrahydropyrido(2,4-d)pyrimidine (IV). When this β-keto-ester is treated with a halogenating agent such as bromine or sulphuryl chloride, it yields a derivative halogenated in the 6-position (V) which is not isolated and which, when treated with an aliphatic tertiary base (for example triethylamine) or an aromatic tertiary base (such as dimethylaniline) or a heterocyclic tertiary base (such as pyridine and its methyl derivatives), undergoes dehydrohalogenation leading to a 6-carbalkoxy-5-oxo-5,8-dihydropyrido(2,3-d)pyrimidine (VI), saponification of which yields the desired acid (I). These reactions may be represented as follows:

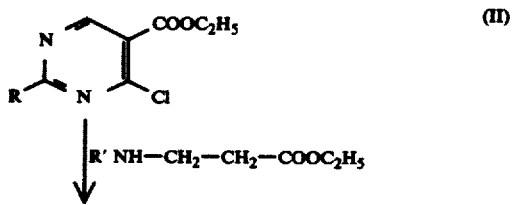

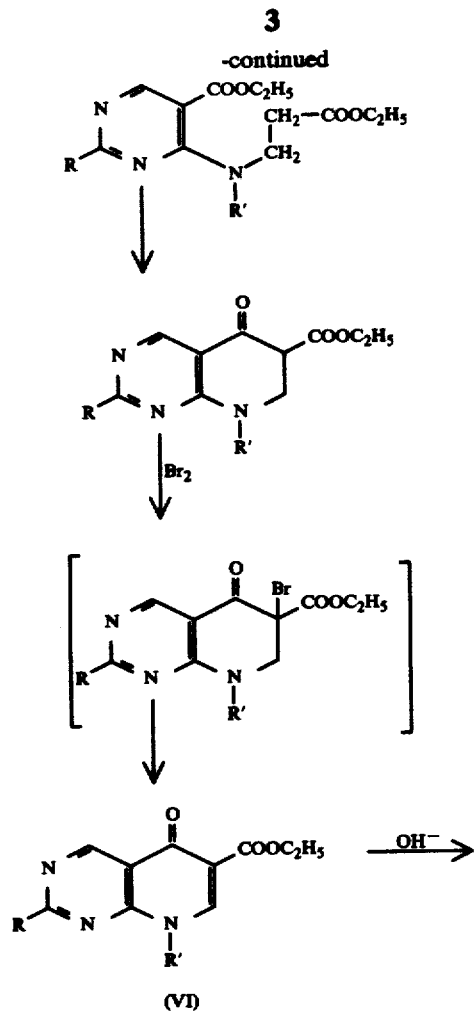

In a modification of this process useful for preparing compounds in which R is —$NR_1R_2$, the starting material is 2,4-dichloro-5-carbethoxy-pyrimidine (II, R = Cl), condensation of which with an N-substituted ethyl β-aminopropionate gives 2-chloro-4-β-carbethoxyethylamino-5-carbethoxy-pyrimidine (VII), which can be used by one of two methods.

In the first method, it is treated under hot conditions with a compound of formula: $HNR_1R_2$, which leads to a $N_2$-substituted 2-amino-4-β-carbethoxyethylamino-5-carbethoxy-pyrimidine (VIII), which, when cyclised by an alkali alcoholate, preferably potassium tertiary butylate, yields the $N_2$-substituted 2-amino-5-oxo-6-carbethoxy-5,6,7,8-tetrahydropyrido(2,3-d)-pyrimidine (IX) which, according to the methods indicated above, leads, after halogenation followed by dehydrohalogenation, to an ester carrying an amine group in the 2-position (X), saponification of which gives the corresponding acid.

In the second method, the 2-chloro-4-β-carbethoxyethylamino-5-carbethoxy-pyrimidine (VIII) is cyclised by a tertiary alkali alcoholate, preferably potassium tertiary butylate to give a 2-chloro-5-oxo-6-carbethoxy-5,6,7,8-tetrahydro-pyrido(2,3-d)pyrimidine (XI), the halogenation followed by dehydrohalogenation of which yields a $N_8$-substituted 2-chloro-6-carbethoxy-5-oxo-5,8-dihydro-pyrido(2,3-d)pyrimidine (XII). The action of a compound of formula $HNR_1R_2$ (generally at ordinary temperature) on the latter leads to an ester (X), saponification of which yields an acid according to the invention. The second method is particularly valuable when the radicals $R_1$ and $R_2$ are sensitive to the halogenation, which leads to the formation of by-products during the stage (IX)→(X).

These reactions may be represented as follows:

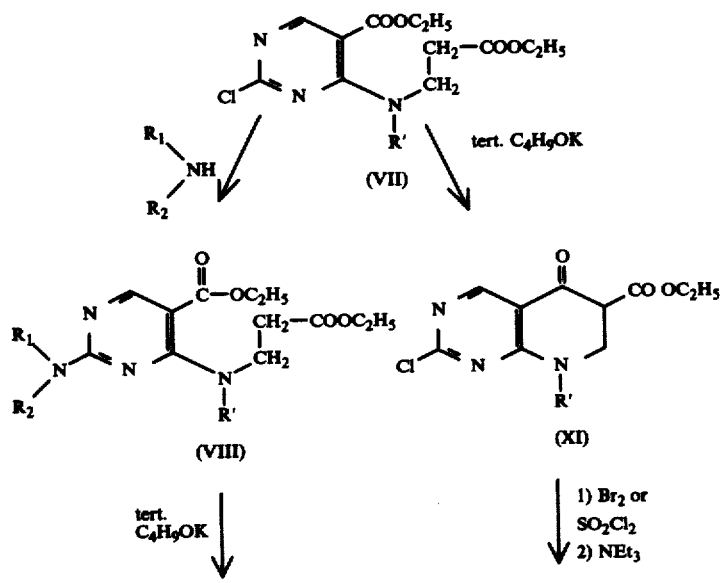

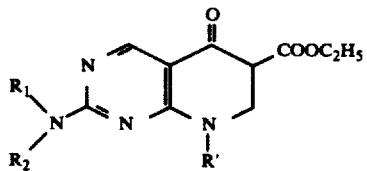
(IX)
1) Br₂
2) NEt₃

-continued

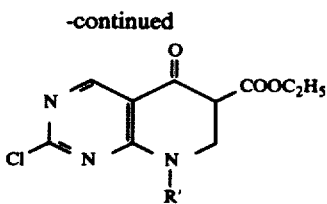
(XII)

NH⟨$^{R_1}_{R_2}$

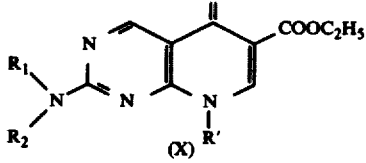
(X)

The condensation of the 4-chloro-5-carbethoxypyrimidines (II) with the N-substituted ethyl β-aminopropionate is carried out at ambient temperature in a neutral solvent such as an aromatic hydrocarbon (benzene or toluene) or a halogenated hydrocarbon (for example chloroform or dichloroethane). Per mol of chloropyrimidine, either two mols of the amino-ester or one mol of the latter and one mol of a tertiary amine (e.g. triethylamine), used as an acceptor of the hydracid formed in the reaction, are employed. After standing for 2 to 10 hours, the solution is filtered, washed with water and dried. Evaporation leaves the ester (III) or (VII), in an approximately theoretical yield, most frequently as an oil which is difficult to crystallise and which can be used directly for the following operation.

One mol of ester (III) or (VII), preferably dissolved in an aromatic hydrocarbon (benzene or toluene), is added at ambient temperature to a solution of potassium tertiary butylate (1 mol), prepared by dissolving 1 gram atom of metal in anhydrous tertiary butanol. The potassium salt of the enolate of the β-keto-ester (IV) or (XI) precipitates from the start of the addition. After standing for at least two hours at ambient temperature, the mixture is taken up in iced water and the aqueous phase is separated by decanting and acidified with acetic acid (1 mol) to cause precipitation of the β-keto-ester which is extracted with a suitable solvent. The organic solution is dried and then evapoated in vacuo: the keto-ester (IV) or (XI) is purified by recrystallisation. The yield is generally between 75 and 80%.

For the halogenation, the ester (IV, IX or XI) is dissolved (at a concentration of, e.g., 10 to 20%) in a suitable solvent such as chloroform or acetic acid. The solution is stirred and cooled externally. One mol of bromine, as a 10% solution in chloroform or acetic acid, is added dropwise, taking care that the temperature remains below 15° C. After standing for 2 hours at ordinary temperature, the solvent is removed at a low temperature (40° C.) in vacuo. The residue is dissolved in 10 parts of chloroform, the solution is cooled, and a solution of 2.5 to 3 mols of a tertiary amine, preferably triethylamine, in the same solvent, is added to it at a temperature of between 10° and 15° C. After contact (2 to 10 hours), the solvent is evaporated in vacuo. The residue is taken up in water and the precipitate is filtered off, washed until the triethylamine hydrobromide has been completely removed, and recrystallised from a suitable solvent. The yields are generally between 75 and 80%. When the halogenation is carried out in chloroform, it is possible to add the tertiary amine directly, under the conditions described above, to the solution resulting from the addition of bromine to the β-keto-ester.

The halogenation can also be carried out with other reagents, especially sulphuryl chloride. The reaction is then preferably carried out in a chloroform solution. The addition of sulphuryl chloride to the solution of the β-keto-ester in equimolar proportions may be carried out at 15°-20° C., and the reaction is completed at ambient temperature within a period of two to four hours. 2.5 to 3 mol proportions of triethylamine or other tertiary amine are then added to the solution which is kept at 10°-15° C., and the dehydrohalogenation reaction is allowed to continue for 4 to 12 hours. The reaction product is isolated and purified as in the case where the halogenating agent is bromine.

The condensation of the 2-chloro-4-(N-β-carbethoxyethyl-N-alkyl)amino-5-carbethoxy-pyrimidine (VII) with the compound $HNR_1R_2$ in a molar ratio of 1:2 is carried out at 70°-100° C., in a neutral solvent with a suitable boiling point, e.g. benzene or toluene. Depending on the reactivity of the compound $HNR_1R_2$, the heating period can be from 1 to 6 hours. After cooling, the hydrochloride of the excess compound $HNR_1R_2$ which has precipitated, is filtered off. Evaporation of the solvent gives the diester (VIII), either in solid form (in which case it is then purified by recrystallisation from a suitable solvent), or as an oil which cannot be crystallised and which is used directly for the following stages. The cyclisation with potassium tertiary butylate and halogenation and dehydrohalogenation of the β-keto-ester (IX) are continued in accordance with the techniques described above.

The condensation of 2-chloro-5-oxo-6-carbethoxy-8-ethyl-5,8-dihydro-pyrido(2,3-d)pyrimidine (XII) (1 mol) with the compound $HNR_1R_2$ can be carried out either by using an excess of the latter, i.e. 2 to 2.5 molar proportions, as an acceptor for the hydracid formed in the reaction, or by employing 1 molar proportion of the compound $HNR_1R_2$ and 1 to 1.5 molar proportions of a tertiary amine, (for example triethylamine), the latter playing the role of acid acceptor. The reaction can be carried out in an aromatic hydrocarbon (e.g. benzene or toluene), a halogenated aliphatic hydrocarbon (e.g. chloroform or dichloroethane) or a lower alcohol (e.g. ethanol or isopropanol).

The compound $HNR_1R_2$, used in excess, or its mixture with the tertiary amine is added to the stirred solution or suspension (usually at 10 to 20% concentration) of the halogenated derivative. In the majority of cases, the reaction is rapid and complete at ordinary temperature. Where necessary, it is completed by heating at 80°–100° C. for 1 to 2 hours. After evaporating the solvent in vacuo, the residue is taken up in water and the precipitate is filtered off and recrystallised from a suitable solvent.

However, under these conditions, it is not practicable to obtain the esters (X) wherein

reacting piperazine with the chlorinated derivative (XII). In effect, in this case, no matter what the experimental conditions may be, the two imine groups of piperazine both react and a mixture of the monosubstituted and disubstituted derivatives is obtained. The desired mono-substituted compound can however be obtained by condensing a chlorinated derivative (XII) with 1-formyl-piperazine: a 2-(4'-formyl-piperazino) derivative

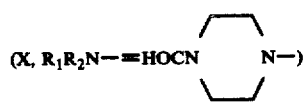

is thus obtained, which can then be deformylated, e.g. by treatment with a solution of hydrogen chloride in ethanol, to give the piperazino derivative

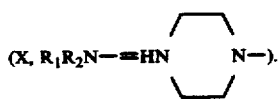

The esters (VI) and (X) may be saponified, most frequently in an aqueous-alcoholic medium, with an alkali metal hydroxide (1.2–1.5 molar proportions). At ordinary temperature, the reaction is generally complete in one to three hours. The excess ethanol is removed by evaporation in vacuo at a low temperature, the residue is dissolved in water, and the solution is rendered slightly acidic (pH 3 to 6). The acid (I) usually precipitates: it is then filtered off, washed and recrystallised from a suitable solvent. If, however, the acid (I) is soluble in water, the solution is saturated with a salt, e.g. by adding sodium chloride or sodium acetate, and the acid is extracted with a suitable solvent such as, for example, chloroform. After evaporating the latter, the acid is recrystallised from a suitable solvent.

Since certain compounds are sensitive to the action of strong bases, the saponification can also be carried out by heating the esters under reflux with a solution of an alkali metal carbonate. After cooling, the acids are isolated as above.

The following Examples illustrate the invention.

EXAMPLE I

5-Oxo-8-ethyl-5,8-dihydro-pyrido(2,3-d)pyrimidine-6-carboxylic acid (I, R = H, R' = $C_2H_5$)

15.2 g. of ethyl N-ethyl-β-aminopropionate are added, with stirring, to a solution of 9.3 g. of 4-chloro-6-carbethoxy-pyrimidine in 75 cm³ of benzene. After standing overnight at ambient temperature, in the absence of moisture (calcium chloride guard tube), the precipitate of the amino-ester hydrochloride is filtered off and the organic solution is washed with water and dried over $Na_2SO_4$. Evaporation of the solvent leaves 14 g. of 4-β-carbethoxyethylamino-5-carbethoxy-pyrimidine as an uncrystallisable oil.

This oil, dissolved in 100 cm³ of benzene, is added with vigorous stirring to a solution of potassium tertiary butylate prepared from 1.2 g. of potassium and 90 cm³ of tertiary butyl alcohol. The potassium derivative of the reaction product precipitates. After standing overnight at ordinary temperature, the mass is taken up in 300 cm³ of iced water, the organic phase is isolated by decanting and the aqueous phase is washed with ether and then acidifed with acetic acid (3 cm³). The precipitate which has formed is filtered off, washed with water and then dissolved in chloroform. After drying over $MgSO_4$, evaporation of the solvent leaves 10 g. of 5-oxo-6-carbethoxy-8-ethyl-5,6,7,8-tetrahydro-pyrido-(2,3-d)pyrimidine which is purified by recrystallisation from isopropyl ether; melting point 124° C. (KOFLER bench).

Analysis for $C_{12}H_{15}N_3O_3$ (molecular weight 249). Calculated %—C, 57.82; H, 6.07; N, 16.86. Found %—C, 57.56; H, 6.17; N, 16.95.

6.25 g. of this β-keto-ester are dissolved in 25 cm³ of chloroform. The solution is stirred vigorously and is cooled externally by a bath of iced water. A solution of 4.1 g. of bromine in 40 cm³ of chloroform is added to it, dropwise, over the course of about 30 minutes. When the addition is complete, the mixture is left for one hour at ambient temperature.

The solution is concentrated to dryness in vacuo at 40° C. The residue is taken up in 20 cm³ of ethanol and 5.4 cm³ of triethylamine are added to the solution. The mixture is heated under reflux for 30 minutes, the solvent is removed in vacuo, the residue is taken up in 100 cm³ of water and the insoluble matter is extracted with chloroform (3 × 50 cm³). The organic solution is dried ($Na_2SO_4$) and decolourised by means of animal charcoal. After evaporating the solvent, the residue is recrystallised from a mixture of isopropyl ether and benzene. 5 g. of 5-oxo-6-carbethoxy-8-ethyl-5,8-dihydro-pyrido(2,3-d)-pyrimidine are obtained. Melting point 136° C.

Analysis for $C_{12}H_{13}N_3O_3$. Calculated %—C, 58.29; H, 5.30; N 17.00. Found %—C, 58.26; H, 5.21; N 17.11.

0.6 g. of this ester and 10 cm³ of a 10% solution of $Na_2CO_3$ are heated under reflux for 20 minutes. After cooling, the solution is acidified by means of acetic acid. The precipitate (0.5 g.) is filtered off and recrystallised from water. 0.2 g. of 5-oxo-8-ethyl-5,8-dihydro-pyrido(2,3-d)pyrimidine-6-carboxylic acid is obtained, melting point 225° C. (decomposition).

Analysis for $C_{10}H_9N_3O_3$ (219.2). Calculated %—C, 54.79; H, 4.14; N, 19.17. Found %—C, 55.05; H, 4.45; N 19.54.

In this Example and in the Examples which follow the acids were dried under vacuum (5 mn) at 150° C. prior to analysis.

EXAMPLE II c1
2-Methylmercapto-5-oxo-8-ethyl-5,8-dihydro-pyrido(2,3-d)pyrimidine-6-carboxylic acid (I, R = $CH_3S$, R' = $C_2H_5$)

A solution of 23.2 g. of 2-methylmercapto-4-chloro-5-carbethoxy-pyrimidine in 100 cm³ of anhydrous benzene is stirred vigorously and a solution of 29 g. of ethyl N-ethyl-β-aminopropionate in 60 cm³ of the same solvent is added to it. After standing overnight at ambient temperature, the hydrochloride of the ester is filtered off; the solution is washed with water, dried and then concentrated to dryness and leaves 3.2 g. of crude 2-methylmercapto-4-β-carbethoxy-ethylamino-5-carbethoxy-pyrimidine as a viscous oil which is used directly for the following stage.

16.5 g. of the crude diester, dissolved in 80 cm³ of anhydrous benzene, are added, with stirring, to a solution of potassium tertiary butylate prepared from 2 g. of potassium and 150 cm³ of tertiary butyl alcohol. The potassium derivative of the cyclisation product precipitates. After standing overnight at ambient temperature, the mass is taken up in 300 cm³ of water. The slightly cloudy aqueous phase is filtered, washed with water and then acidifed with 3 cm³ of acetic acid. The precipitate is extracted with chloroform, the organic solution is dried over $Na_2SO_4$, the solvent is evaporated and the residue is recrystallised from ethanol. 6.5 g. of 2-methyl-mercapto-5-oxo-6-carbethoxy-8-ethyl-5,6,7,8-tetrahydro-pyrido(2,3-d)pyrimidine are obtained; melting point 157° C.

Analysis for $C_{13}H_{17}N_3O_3S$ (molecular weight 295.29). Calculated %—C, 52.87; H, 5.80; N 14.23. Found %—C, 52.84; H, 5.65; N 14.35.

A solution of 3.7 g. of bromine in 40 cm³ of chloroform is added, as described in Example I (duration of the addition: 15 minutes), to a solution of 6.3 g. of the above β-keto-ester in 50 cm³ of chloroform. After stirring for 1 hour 30 minutes at ambient temperature, the reaction product is isolated as described in Example I. It is dissolved in 40 cm³ of ethanol and 9 cm³ of triethylamine are added to it. The mixture is heated under reflux for 30 minutes and the solvent is evaporated in vacuo. The residue is taken up in 50 cm³ of water and the insoluble matter is extracted with 2 × 50 cm³ of chloroform. The organic solution is dried over $MgSO_4$, the solvent is evaporated and the residue is recrystallised from ethanol. 4.5 g. (72%) of 2-methylmercapto-5-oxo-6-carbethoxy-8-ethyl-pyrido(2,3-d)pyrimidine are obtained; melting point 148° C.

Analysis for $C_{13}H_{15}N_3O_3S$ (molecular weight 293.27). Calculated %—C, 53.24; H, 5.16; N 14.33. Found %—C, 53.56; H, 5.26; N, 14.23.

1 g. of the above ester and 15 cm³ of a 10% strength solution of $Na_2CO_3$ are heated under reflux for 45 minutes. The solution is acidified with acetic acid. The precipitate is filtered off, washed with water and recrystallised from dimethylformamide. 0.4 g. of 2-methyl-mercapto-5-oxo-8-ethyl-5,8-dihydro-pyrido(2,3-d)-pyrimidine-6-carboxylic acid is obtained. Melting point 258° C.

Analysis for $C_{11}H_{11}N_3O_3S$ (molecular weight 265.22). Calculated %—C, 49.81; H, 4.18; N, 15.84. Found %—C, 49.88; H, 4.41; N, 16.42.

EXAMPLE III
2-Pyrrolidino-5-oxo-8-ethyl-5,8-dihydro-pyrido(2,3-d)-pyrimidine-6-carboxylic acid (I, R = $C_4H_8N$, R' = $C_2H_5$)

A solution of 50 g. of 2,4-dichloro-5-carbethoxypyrimidine in 250 cm³ of benzene is stirred and cooled externally by means of an ice bath. A solution of 70 g. of ethyl N-ethyl-β-aminopropionate dissolved in 70 cm³ of benzene is added to it, dropwise, and the addition is carried out at a rate such that the temperature of the mixture remains between 10° and 15° C. (duration 1 hour to 1 hour 30 minutes). The reaction is continued for a further 3 hours at ordinary temperature.

Ethyl N-ethyl-β-ethylaminopropionate hydrochloride is filtered off and the solvent is driven off in vacuo. The residue is taken up in 200 cm³ of ether to remove a small amount of hydrochloride. The solution is filtered and evaporated and 70 g. of 2-chloro-4-β-carbethoxyethylamino-5-carbethoxy-pyrimidine are obtained as a viscous oil which is used directly for the subsequent operations.

11 g. of 2-chloro-4-β-carbethoxyethylamino-5-carbethoxy-pyrimidine, 4.7 g. of pyrrolidine and 75 cm³ of anhydrous benzene are heated under reflux for 6 hours. After cooling, the solution is filtered and concentrated to dryness. The oil obtained (11 g.), dissolved in 75 cm³ of benzene, is added to a solution of potassium tertiary butylate prepared from 1.2 g. of potassium and 50 cm³ of tertiary butyl alcohol. After standing overnight at ordinary temperature, the mass is taken up in 200 cm³ of iced water. The aqueous phase is acidified with 2.5 cm³ of acetic acid. The precipitate is extracted with chloroform. After drying over $Na_2SO_4$, the solvent is evaporated and the residue is recrystallised from isopropyl ether and yields 3 g. of 2-pyrrolidino-5-oxo-6-carbethoxy-8-ethyl-5,6,7,8-tetrahydro-pyrido(2,3-d)pyrimidine; melting point 120° C.

Analysis for $C_{16}H_{22}N_4O_3$ (molecular weight 318.37). Calculated %—C, 60.36; H, 6.97; N, 17.60. Found %—C, 60.12; H, 7.26; N, 17.68.

A solution of 0.6 g. of bromine in 5 cm³ of acetic acid is added, with stirring and cooling, to 1.06 g. of this β-keto-ester, dissolved in 10 cm³ of acetic acid. After standing for 1 hour at ambient temperature, the solvent is evaporated in vacuo at 40° C. The residue is dissolved in 10 cm³ of ethanol, 1.4 cm³ of triethylamine are added to the solution and the mixture is heated under reflux for 30 minutes. After evaporating the solvent, the residue is taken up in 20 cm³ of water and the insoluble matter is extracted with chloroform. After drying and evaporating the solvent, recrystallisation of the residue from ethanol yields 0.76 g. (76%) of 2-pyrrolidino-5-oxo-6-carbethoxy-8-ethyl-5,8-dihydropyrido(2,3-d)pyrimidine; melting point = 202° C.

Analysis for $C_{16}H_{20}N_4O_3$ (molecular weight 316.35). Calculated %—C, 60.74; H, 6.37; N, 17.71. Found %—C, 60.39; H, 6.17; N, 17.53.

0.9 g. of this ester and 20 cm³ of a 10% solution of $Na_2CO_3$ are heated under reflux for 3 hours. The reaction product is isolated as described in Example II. After recrystallisation from dimethylformamide, 0.37 g. of 2-pyrrolidino-5-oxo-8-ethyl-5,8-dihydro-pyrido(2,3- d)-pyrimidine-6-carboxylic acid is obtained; melting point 314°–316° C. (Maquenne block).

Analysis for $C_{14}H_{16}N_4O_3$ (molecular weight 288.3) Calculated %—C, 58.32; H, 5.59; N 19.44. Found %—C, 58.02; H, 5.68; N, 19.50.

EXAMPLE IV 2-(4'-Hydroxy-piperidino)-5-oxo-8-ethyl-5,8-dihydropyrido(2,3-d)pyrimidine-6-carboxylic acid

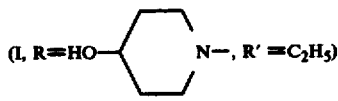

(I, R=HO—⟨ ⟩—N—, R' =C₂H₅)

In a 1 liter 3-necked flask equipped with a mechanical stirrer, a dropping funnel and a thermometer, a solution of potassium tertiary butylate is prepared from 400 cm³ of the tertiary alcohol and 8 g. of potassium metal. This solution is brought to 20° C. and 66 g. of 2-chloro-4-β-carbethoxyethylamino-5-carbethoxypyrimidine are added to it and the mixture is stirred at ordinary temperature for 2 hours: the potassium derivative of the reaction product precipitates. The mixture is poured into 200 cm³ of iced water and the solution is brought to pH 3 by adding 4N hydrochloric acid with stirring. The precipitate is filtered off, washed with water and recrystallised from 320 cm³ of isopropanol and yields 46 g. (81.2%) of 2-chloro-5-oxo-6-carbethoxy-8-ethyl-5,6,7,8-tetrahydro-pyrido(2,3-d)-pyrimidine; melting point 146° C.

Analysis for $C_{12}H_{14}ClN_3O_3$ (molecular weight 283.5). Calculated %—C, 50.79; H, 5.07; N, 14.81; Cl, 12.50. Found %—C, 51.10; H, 5.14; N, 14.61; Cl, 12.68.

64 g. (0.22 mol) of the above β-keto-ester are dissolved in 250 cm³ of chloroform. The solution is cooled in a bath of iced water and a solution of bromine (35.1 g., 0.44 gram atom) in 300 cm³ of chloroform is added to it at a rate such that the temperature of the reaction mixture remains between 10° and 15° C., which takes about 2 hours. The solution is stirred for a further hour at ambient temperature, the solvent is driven off in vacuo and the residue is taken up in 200 cm³ of anhydrous chloroform. The solution is stirred in a bath of iced water and a solution of triethylamine (50 g, 0.48 mol) in 100 cm³ of chloroform is added to it, dropwise, at a rate such that the temperature of the mixture remains between 15° and 10° C. (duration 2 hours).

When the addition is complete, the solution is stirred for a further hour at 20° C., the solvent is evaporated in vacuo and the residue is taken up in 200 cm³ of water. The insoluble matter is extracted with benzene and the organic solution is dried over MgSO₄.

Evaporation of the solvent leaves a residue which, after recrystallisation from 450 cm³ of a mixture of isopropyl ether (1 volume) and benzene (1 volume), yields 50 g. (78.1%) of 2-chloro-5-oxo-6-carbethoxy-5,8-dihydro-pyrido(2,3-d)pyrimidine; melting point 158° C.

Analysis for $C_{12}H_{12}ClN_3O_3$ (molecular weight 281.5). Calculated %;13 C, 51.15; H, 4.26; N, 14.91; Cl, 12.61. Found %—C, 51.32; H, 4.52; N, 14.84; Cl, 12.50.

3.5 g. of 2-chloro-5-oxo-6-carbethoxy-8-ethyl-pyrido(2,3-d)pyrimidine, dissolved in 15 cm³ of chloroform, are cooled and stirred at −5° C. 1.7 g. of sulphuryl chloride, dissolved in 10 cm³ of anhydrous chloroform, are added. The cooling mixture is removed and the solution is stirred at ordinary temperature for 2 hours. It is again cooled to 5°–10° C., and a solution of 5.5 cm³ of triethylamine in 10 cm³ of chloroform is added to it, dropwise. The mixture is left to stand overnight at ambient temperature. The solvent is evaporated and the residue is taken up in 50 cm³ of water. The precipitate is filtered off, washed with water and dissolved in 50 cm³ of ethyl acetate. The solution is dried (MgSO₄), the solvent is evaporated and the residue is recrystallised from a mixture of isopropyl ether and benzene. 2.2 g. (63%) of 2-chloro-5-oxo-6-carbethoxy-8-ethyl-5,8-dihydropyrido(2,3-d)pyrimidine are obtained; melting point 156° C. (identical to the product described above).

2.8 g. of 2-chloro-5-oxo-6-carbethoxy-8-ethyl-5,8-dihydro-pyrido(2,3-d)pyrimidine and 2 g. of 4-hydroxypiperidine, dissolved in 35 cm³ of toluene, are heated under reflux for 4 hours. After cooling, 20 cm³ of water are added to the mixture; the organic phase is washed again with water and dried over MgSO₄; the solvent is evaporated and the residue is recrystallised from ethanol and yields 1.75 g. of 2-(4'-hydroxy-piperidino)-5-oxo-6-carbethoxy-5,8-dihydro-pyrido(2,3-d)pyrimidine; melting point 205° C.

Analysis for $C_{17}H_{22}N_4O_4$ (molecular weight 346.38). Calculated %—C, 58.94; H, 6.40; N, 16.18. Found %—C, 59.00; H, 6.30; N, 16.12.

1.75 g. of this ester are added to a solution of sodium hydroxide (0.25 g.) in a mixture of alcohol (30 cm³) and water (2 cm³). The mixture is stirred for one hour at ambient temperature, the solvent is driven off in vacuo and the residue is dissolved in 10 cm³ of water. The solution is acidifed by means of acetic acid. The precipitate is filtered off, washed with water and recrystallised from ethanol and yields 0.6 g. of 2-(4'-hydroxy-piperidino)-5-oxo-8-ethyl-5,8-dihydropyrido(2,3-d)pyrimidine-6-carboxylic acid. Melting point 244° C.

Analysis for $C_{15}H_{18}N_4O_4$ (molecular weight 318.33). Calculated %—C, 56.59; H, 5.70; N, 17.60. Found %—C, 56.37; H, 5.95; N, 17.47.

EXAMPLE V 2-(4'-Methyl-piperazino)-5-oxo-5,8-dihydro-pyrido(2,3-d)pyrimidine-6-carboxylic acid

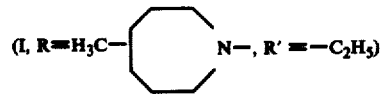

(I, R=H₃C—⟨ ⟩—N—, R' =—C₂H₅)

8.4 g. (0.03 mol) of 2-chloro-5-oxo-6-carbethoxy-8-ethyl-5,8-dihydro-pyrido(2,3-d)pyrimidine, suspended in 60 cm³ of ethanol, are stirred vigorously. A mixture of 3.3 g. (0.03 mol) of 1-methyl-piperazine and 3.3 g. of triethylamine, dissolved in 20 cm³ of ethanol, is added rapidly. The chlorinated derivative dissolves with evolution of heat. After stirring for 2 hours at ambient temperature, the solvent is driven off in vacuo, the residue is taken up in 50 cm³ of a saturated solution of Na₂CO₃ and the mixture is extracted with chloroform. After drying (Na₂SO₄) and evaporation, the residue (9.5 g.) is recrystallised from 100 cm³ of a mixture of isopropyl ether (1 volume) and benzene (1 volume) and yields 8.5 g. (85%) of 2-(4'-methyl-piperazino)-5-oxo-6-carbethoxy-8-ethyl-pyrido(2,3-d)pyrimidine which melts in two stages: 146° C. and then 158° C.

Analysis for $C_{17}H_{23}N_5O_3$ (molecular weight 345.39). Calculated %—C, 59.11; H, 6.71; N, 20.28. Found %—C, 59.23; H, 6.68; N, 20.42.

25.3 g. of this ester (0.075 mol) are stirred with 100 cm³ of N NaOH solution. The solution is heated to 50°-60° C., to dissolve the ester and then the saponification is completed at ambient temperature over the course of 2 hours. The solution is brought to pH 6 with acetic acid. After saturating the mixture with sodium acetate, the solution is extracted with 4 × 50 cm³ of chloroform.

The combined chloroform extracts are dried over $MgSO_4$, the solvent is evaporated and the residue is recrystallised from a mixture of ethanol (500 cm³) and dimethylformamide (100 cm³); 14.5 g. of acid are thus obtained. On concentrating the crystallisation mother liquors to ⅓ of their volume, a further 1.5 g. of product are obtained, corresponding to a total yield of 16 g. (70%). 2-(4'-Methyl-piperazino)-5-oxo-8-ethyl-5,8-dihydro-pyrido(2,3-d)pyrimidine-6-carboxylic acid melts 227° C.

Analysis for $C_{15}H_{19}N_5O_3$ (molecular weight 317.34). Calculated %—C, 56.77; H, 6.04; N, 22.07. Found %—C, 56.69; H, 6.23; N, 22.35.

EXAMPLE VI 2-(4-β-Hydroxyethyl-piperazino)-5-oxo-8-ethyl-5,8-dihydropyrido(2,3-d)pyrimidine-6-carboxylic acid

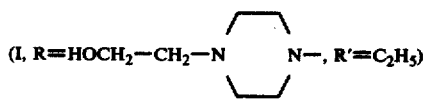

(I, R=$HOCH_2$—$CH_2$—N  N—, R'=$C_2H_5$)

5.6 g. of 2-chloro-5-oxo-6-carbethoxy-8-ethyl-5,8-dihydro-pyrido(2,3-d)pyrimidine, 5.2 g. of 1-β-hydroxyethyl piperazine and 50 cm³ of toluene are heated under reflux for 2 hours. After cooling, the solution is filtered to remove the hydrochloride which has precipitated, and the organic solution is diluted with its own volume of chloroform, is washed with water and dried ($MgSO_4$). After evaporation, the residue is recrystallised from 40 cm³ of a mixture of isopropanol (1 volume) and isopropyl ether (2 volumes). 5.14 g. (68%) of 2-(4'-β-hydroxyethyl-piperazino)-5-oxo-6-carbethoxy-8-ethylpyrido(2,3-d)pyrimidine are obtained; melting point 172° C.

Analysis for $C_{18}H_{25}N_5O_4$ (molecular weight 375.42). Calculated %—C, 57.58; H, 6.71; N, 18.60. Found %—C, 57.53; H, 6.57; N, 18.80.

5.14 g. of the ester are added to an aqueous-alcoholic solution of sodium hydroxide (N NaOH: 15 cm³, ethanol: 10 cm³); the mixture is stirred for 2 hours at ordinary temperature and is then brought to pH 6 by adding acetic acid. After concentration to dryness in vacuo, the residue is taken up in a saturated solution of sodium acetate (50 cm³) and is extracted with chloroform (3 × 50 cm³). After drying ($MgSO_4$), the solvent is evaporated and the residue is recrystallised from 80 cm³ of ethanol. 2.4 g. (53.3%) of 2-(4'-β-hydroxyethyl-piperazino)-5-oxo-8-ethyl-5,8-dihydro-pyrido(2,3-d)pyrimidine-6-carboxylic acid are obtained; melting point 222° C.

Analysis for $C_{16}H_{21}N_5O_4$ (molecular weight 347.37). Calculated %—C, 55.32; H, 6.09; N, 20.16. Found %—C, 54.96; H, 6.04; N, 19.92.

EXAMPLE VII 2-(4'-Benzyl-piperazino)-5-oxo-8-ethyl-5,8-dihydropyrido(2,3-d)pyrimidine-6-carboxylic acid

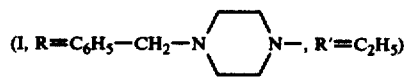

(I, R=$C_6H_5$—$CH_2$—N  N—, R'=$C_2H_5$)

As described in Example VI, a mixture of 5.6 g. of 2-chloro-5-oxo-6-carbethoxy-8-ethyl-5,8-dihydropyrido(2,3-d)pyrimidine, 7.04 g. of N-benzylpiperazine and 80 cm³ of toluene is heated under reflux for 2 hours. After cooling, the mass is diluted with 100 cm³ of chloroform and is taken up in 200 cm³ of water. After washing the organic phase with water, the reaction product is isolated as described in the Example mentioned. It is recrystallised from isopropanol. 7.6 g. (90%) of 2-(4'-benzyl-piperazino)-5-oxo-6-carbethoxy-8-ethyl-5,8-dihydro-pyrido(2,3-d)pyrimidine are obtained; melting point 152° C.

Analysis for $C_{23}H_{27}N_5O_3$ (molecular weight 421.49). Calculated %—C, 65.54; H, 6.46; N, 16.62. Found %—C, 66.03; H, 6.44; N, 16.97.

Saponification of 9.5 g. of this ester with an aqueous-alcoholic solution of sodium hydroxide (N NaOH, 15 cm³ + water, 30 cm³ + ethanol, 30 cm³) is complete in 1 hour at ordinary temperature. After acidification, the precipitate is filtered off and recrystallised from 160 cm³ of a mixture of dimethylformamide (1 volume) and ethanol (1 volume). 6.8 g. of 2-(4'-benzyl-piperazino)-5-oxo-8-ethyl-5,8-dihydro-pyrido(2,3-d)pyrimidine-6-carboxylic acid are obtained; melting point 207° C.

Analysis for $C_{21}H_{23}N_5O_3$ (molecular weight 293.43). Calculated %—C, 64.11; H, 5.89; N, 17.80. Found %—C, 64.42; H, 6.03; N, 17.79.

EXAMPLE VIII

2-Piperazino-5-oxo-8-ethyl-5,8-dihydro-pyrido(2,3-d)pyrimidine-6-carboxylic acid

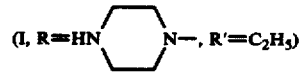

(I, R=HN  N—, R'=$C_2H_5$)

A mixture of 8.4 g of 2-chloro-6-oxo-6-carbethoxy-8-ethyl-5,8-dihydro-pyrido(2,3-d)pyrimidine, 6.9 g of formylpiperazine and 160 cm³ of chloroform is heated under reflux for one hour. After cooling, the solution is washed with water and dried and the solvent is evaporated. The oily residue crystallises on being taken up in 100 cm³ of isopropyl ether. The solid is filtered off and recrystallised from 60 cm³ of ethanol and yields 8.9 g (82%) of 2-(4'-formylpiperazino)-5-oxo-6-carbethoxy-8-ethyl-5,8-dihydro-pyrido(2,3-d)pyrimidine which melts in two stages; melting point 195° C., solidification, followed by m.p. 204° C.

Analysis for $C_{17}H_{21}N_5O_4$ (molecular weight 359.38). Calculated %—C, 56.81; H, 5.89; N, 19.49. Found %—C, 56.97; H, 5.95; N, 19.58.

3.6 g of the above formyl derivative are suspended in 25 cm³ of a 5% strength solution of HCl in alcohol. After gentle heating (at 40°-50° C.) to facilitate dissolution, the mixture is left to stand for 8 hours at ordinary temperature. The dihydrochloride of the deformylated derivative precipitates. After being taken in 100 cm³ of ether, it is filtered off and suspended in 40 cm³ of water and the mixture, having been rendered alkaline by adding Na₂CO₃, is extracted with chloroform. After evaporating the solvent, the product is recrystallised from 40 cm³ of a mixture of isopropyl ether (1 volume) and benzene (1 volume). 2.8 g (84%) of 2-piperazino-5-oxo-6-carbethoxy-8-ethyl-5,8-dihydro-pyrido(2,3-d)pyrimidine are obtained; melting point 155° C.

Analysis for $C_{16}H_{21}N_5O_3$ (molecular weight 331.37). Calculated %—C, 57.99; H, 6.39; N, 21.14. Found %—C, 57.98; H, 6.23; N, 21.39.

Saponification of this ester (3.3 g) with 30 cm³ of N/3 aqueous sodium hydroxide solution is complete in 2 hours at ordinary temperature. After acidification (pH about 6) with acetic acid, the precipitate is filtered off, washed with water and recrystallised from 60 cm³ of a mixture of dimethylformamide (1 volume) and ethanol (1 volume). 1.8 g of 2-piperazino-5-oxo-8-ethyl-5,8-dihydropyrido(2,3-d)pyrimidine-6-carboxylic acid are obtained; melting point 264° C.

Analysis for $C_{14}H_{17}N_5O_3$ (molecular weight 303.32). Calculated %—C, 55.43; H, 5.65; N, 23.09. Found %—C, 55.68; H, 5.67; N, 23.25.

EXAMPLE IX 2-(4'-Phenyl-piperazino)-5-oxo-5,8-dihydro-pyrido(2,3-d)-pyrimidine-6-carboxylic acid

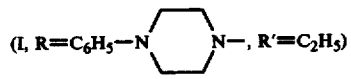

A solution of 3.2 g (0.02 mol) of N-phenyl-piperazine in 30 cm³ of toluene is added to 2.8 g (0.01 mol) of 2-chloro-5-oxo-6-carbethoxy-8-ethyl-5,8-dihydro-pyrido(2,3-d)-pyrimidine dissolved in 30 cm³ of toluene. Reaction takes place practically instantaneously with evolution of heat and the mixture sets solid due to formation of phenylpiperazine hydrochloride. The mixture is diluted with 100 cm³ of ethyl acetate, the solution is filtered, washed with water and dried (MgSO₄) and the solvent is evaporated. The residue is recrystallised from 110 cm³ of isopropanol and yields 3.38 g (84%) of 2-(4'-phenyl-piperazino)-5-oxo-6-carbethoxy-8-ethyl-5,8-dihydro-pyrido(2,3-d)pyrimidine; melting point 186° C.

Analysis for $C_{22}H_{25}N_5O_3$ (molecular weight 407.46). Calculated %—C, 64.85; H, 6.18; N, 17.19. Found %—C, 64.97; H, 6.08; N, 16.74.

When 2 g of this ester are saponified as indicated in Example VIII, they yield, after acidification and recrystallisation of the precipitate from 90 cm³ of a mixture of dimethylformamide (1 volume) and ethanol (1 volume), 1.4 g (77%) of 2-(4'-phenyl-piperazino)-5-oxo-5,8-dihydro-pyrido(2,3-d)pyrimidine-6-carboxylic acid; melting point 249° C.

Analysis for $C_{20}H_{21}N_5O_3$ (molecular weight 379.41). Calculated %—C, 63.31; H, 5.58; N, 18.46. Found %—C, 63.49; H, 5.71; N, 18.36.

EXAMPLE X 2-(4'-Methyl-piperazino)-5-oxo-8-methyl-5,8-dihydropyrido-(2,3-d)pyrimidine-6-carboxylic acid

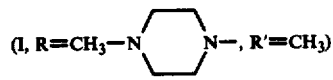

26.2 g of ethyl N-methyl-β-aminopropionate, dissolved in 150 cm³ of benzene, are added dropwise to a solution, which is stirred and cooled to between 10° and 15° C.; of 22 g of 2,4-dichloro-carbethoxypyrimidine in 150 cm³ of the same solvent. After standing overnight, the solvent is evaporated in vacuo and the residue is taken up in water (100 cm³) and extracted with ether. The organic solution is washed with water, dried (MgSO₄) and evaporated. The residue is recrystallised from 60 cm³ of hexane and yields 25 g (80%) of 2-chloro-4-(N-β-carbethoxyethyl-N-methyl)amino-5-carboethoxy-pyrimidine; melting point 60° C.

Analysis for $C_{13}H_{18}ClN_3O_4$ (molecular weight 315.5). Calculated %—C, 49.45; H, 5.74; N, 13.31. Found %—C, 49.80; H, 6.07; N, 13.21.

A solution of 10.5 g of this diester in 100 cm³ of benzene is added, with stirring and in the absence of moisture, to a solution of potassium tertiary butylate prepared from 1.4 g of potassium metal and 80 cm³ of tertiary butanol. The potassium derivative of the reaction product precipitates in the medium, which sets solid. After 2 hours at ordinary temperature, 2.5 cm³ of acetic acid followed by 300 cm³ of iced water are added, with stirring. The benzene phase is isolated by decanting, washed with water and dried (MgSO₄) and the solvent is evaporated. The residue is recrystallised from benzene and yields 5.7 g (63%) of 2-chloro-5-oxo-6-carbethoxy-8-methyl-5,6,7,8-tetrahydro-pyrido(2,3-d)pyrimidine; melting point 175° C.

Analysis for $C_{11}H_{12}ClN_3O_3$ (molecular weight 269.68). Calculated %—C, 48.98; H, 4.48; N, 15.58; Cl, 13.14. Found %—C, 49.00; H, 4.70; N, 15.34; Cl, 13.10.

A solution of 14 g of this β-keto-ester, dissolved in 100 cm³ of chloroform, is stirred and cooled to 10° C. A solution of 2.8 cm³ of bromine in 100 cm³ of chloroform is added to it, dropwise, at a rate such that the temperature of the reaction mixture remains between 10° and 15° C. The solution is left to stand at ambient temperature for 1 hour and is again cooled to 10° C., and a solution of triethylamine (16 cm³) in chloroform (100 cm³) is added to it dropwise.

After standing overnight at ordinary temperature, the solvent is removed in vacuo at 40° C. The residue is taken up in water (100 cm³), filtered off, washed to remove the triethylamine hydrobromide and dissolved again in chloroform (100 cm³); the solution is dried (MgSO₄), the solvent is evaporated and the residue is recrystallised from a mixture of isopropyl ether and benzene. 9.16 g (65.5%) of 2-chloro-5-oxo-6-carbethoxy-8-methyl-5,8-dihydro-pyrido(2,3-d)pyrimidine are obtained; melting point 205° C.

Analysis for $C_{11}H_{10}ClN_3O_3$ (molecular weight 267.67). Calculated %—C, 49.34; H, 3.76; N, 15.69; Cl, 13.24. Found %—C, 49.42; H, 3.95; N, 15.46; Cl, 13.02.

1.5 g of N-methylpiperazine are added to a stirred suspension of 2 g of 2-chloro-5-oxo-6-carbethoxy-8-methyl-5,8-dihydro-pyrido(2,3-d)pyrimidine in 20 cm³ of absolute ethanol. The reaction takes place with evolution of heat. After standing for 2 hours at room temperature, the solvent is evaporated in vacuo, the residue is taken up in water and the precipitate is filtered off, washed, dried in vacuo and recrystallised from benzene: 1.4 g (58%) of 2-(4'-methyl-piperazino)-5-oxo-6-carbethoxy-8-methyl-5,8-dihydro-pyrido(2,3-d)pyrimidine are obtained.

Analysis for $C_{16}H_{21}N_5O_3$ (molecular weight 331.37). Calculated %—C, 57.99; H, 6.39; N, 21.14. Found %—C, 58.50; H, 6.22; N, 21.37.

1.1 g of this ester are saponified by stirring for 2 hours at ordinary temperature in an aqueous-alcoholic solution of sodium hydroxide (NaOH 0.15 g, water 2 cm$^3$, ethanol 5 cm$^3$). The solvents are evaporated at 40° C. in vacuo, the residue is taken up in 20 cm$^3$ of water and the solution is acidified with acetic acid and then extracted with chloroform. Evaporation of the solvent leaves a residue which, after recrystallisation from a mixture of alcohol and dimethylformamide, yields 0.5 g of 2-(4'-methyl-piperazino)-5-oxo-8-methyl-5,8-dihydro-pyrido(2,3-d)pyrimidine-6-carboxylic acid; melting point 280° C.

Analysis for $C_{14}H_{17}N_5O_3$ (molecular weight 303.32). Calculated %—C, 55.43; H, 5.65; N, 23.09. Found %—C, 55.25; H, 5.67; N, 23.24.

EXAMPLE XI 2-(4'-β-Hydroxyethyl-piperazino)-5-oxo-8-methyl-5,8-dihydropyrido(2,3-d)pyrimidine-6-carboxylic acid.

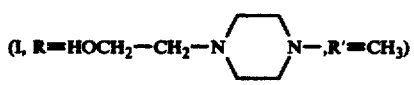

(I, R=HOCH$_2$—CH$_2$—N N—, R'=CH$_3$)

As described in Example X, reaction of N-β-hydroxyethyl-piperazine (2.1 g) with a suspension of 2 g of 2-chloro-5-oxo-6-carbethoxy-8-methyl-5,8-dihydro-pyrido(2,3-d)pyrimidine in 20 cm$^3$ of ethanol (for 2 hours at ordinary temperature) yields, after evaporation of the solvent, a residue which is recrystallised from water, 2.14 g of 2-(4-β-hydroxyethyl-piperazino)-5-oxo-6-carbethoxy-8-methyl-5,8-dihydro-pyrido(2,3-d)pyrimidine dihydrate are obtained; it has two melting points: melting point 160° C., solidification, followed by melting point 170° C.

Analysis for $C_{17}H_{23}N_5O_4 \cdot 2 H_2O$ (molecular weight 397.43) Calculated %—C, 51.37; H, 6.85; N, 17.62. Found %—C, 51.60; H, 6.53; N, 18.01.

1.94 g of this ester are saponified for 2 hours at ordinary temperature (NaOH 0.25 g, water 5 cm$^3$, ethanol 10 cm$^3$). After evaporating the solvent in vacuo, the residue is taken up in 20 cm$^3$ of water and the solution is brought to pH 6 by adding acetic acid. The precipitate is filtered off, washed with water and recrystallised from a mixture of ethanol (1 volume) and dimethylformamide (2 volumes). 1.25 g of 2-(4,β-hydroxyethyl-piperazino)-5-oxo-8-methyl-5,8-dihydro-pyrido(2,3-d)pyrimidine-6-carboxylic acid are obtained; melting point 245° C.

Analysis for $C_{15}H_{19}N_5O_4$ (molecular weight 333.34). Calculated %—C, 54.04; H, 5.75; N, 21.01. Found %—C, 54.14; H, 5.88; N, 21.21.

EXAMPLE XII 2-(4'-Ethyl-piperazino)-5-oxo-8-ethyl-5,8-dihydro-pyrido(2,3-d)pyrimidine-6-carboxylic acid.

(I, R=H$_5$C$_2$—N N—, R'=C$_2$H$_5$)

3.8 g of 2-chloro-5-oxo-6-carbethoxy-8-ethyl-5,8-dihydro-pyrido(2,3-d)pyrimidine and 2.9 g of 1-ethyl-piperazine, dissolved in 50 cm$^3$ of chloroform, are heated under reflux for 2 hours. After cooling, the organic solution is washed with water and dried over MgSO$_4$; the solvent is evaporated and the residue is recrystallised from a mixture of isopropyl ether (15 cm$^3$) and benzene (25 cm$^3$) and gives 4.4 g (yield: 93%) of 2-(4'-ethylpiperazino)-5-oxo-8-ethyl-6-carbethoxy-5,8-dihydro-pyrido(2,3-d)pyrimidine; melting point 161° C.

Analysis for $C_{18}H_{25}N_5O_3$ (359.42). Calculated %—C, 60.15; H, 7.01; N, 19.49. Found %—C, 60.22; H, 6.81; N, 19.66.

Saponification of this ester (3.6 g) with a 2N solution of sodium hydroxide in alcohol, at ordinary temperature, yields, after the treatments described in the preceding examples, 2.23 g (67%) of 2-(4'-ethylpiperazino)-5-oxo-8-ethyl-5,8-dihydro-pyrido(2,3-d)pyrimidine-6-carboxylic acid; melting point 229° C., after recrystallisation from a mixture of ethanol (1 volume) and dimethylformamide (1 volume).

Analysis for $C_{16}H_{21}N_5O_3$ (molecular weight 331.37). Calculated %—C, 57.99; H, 6.39; N, 21.14. Found %—C, 58.27; H, 6.39; N, 21.14.

EXAMPLE XIII 2-(4'-Propyl-piperazino)-5-oxo-8-ethyl-5,8-dihydro-pyrido(2,3-d)pyrimidine-6-carboxylic acid.

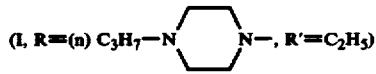

(I, R=(n) C$_3$H$_7$—N N—, R'=C$_2$H$_5$)

As described in Example XII, the condensation of 2.8 g of 2-chloro-5-oxo-6-carbethoxy-8-ethyl-5,8-dihydropyrido(2,3-d)pyrimidine with 2.2 g of 1-propyl-piperazine, in chloroform (40 cm$^3$) gives, after the treatments described in Example XII, 3.14 g of 2-(4'-propyl-piperazino)-5-oxo-6-carbethoxy-8-ethyl-5,8-dihydro-pyrido(2,3-d)pyrimidine (yield 84%); melting point 149° C., after recrystallisation from ethyl acetate.

Analysis for $C_{19}H_{27}N_5O_3$ (molecular weight 373.45). Calculated %—61.10; H, 7.29; N, 18.75. Found %—C, 61.50; H, 7.22; N, 18.91.

Saponification of this ester (2 g) as indicated in the preceding examples, yields, after recrystallisation from a mixture of ethanol (1 volume) and dimethylformamide (2 volumes), 1.32 g (71%) of 2-(4'-propyl-piperazino)-5-oxo-8-ethyl-5,8-dihydro-pyrido(2,3-d)pyrimidine-6-carboxylic acid; melting point 226° C.

Analysis for $C_{17}H_{23}N_5O_3$ (molecular weight 345.39). Calculated %—C, 59.11; H, 6.71; N, 20.28. Found %—C, 58.75; H, 6.73; N, 20.00.

EXAMPLE XIV 2-(4'-Allyl-piperazino)-5-oxo-8-ethyl-5,8-dihydro-pyrido(2,3-d)pyrimidine-6-carboxylic acid.

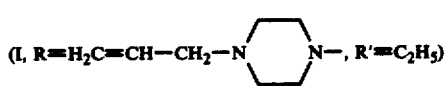

(I, R=H₂C=CH—CH₂—N⟩N—, R'=C₂H₅)

2-(4'-Allyl-piperazino)-5-oxo-6-carbethoxy-8-ethyl-5,8-dihydro-pyrido(2,3-d)pyrimidine is prepared, in a yield of 79%, by condensing 2-chloro-5-oxo-6-carbethoxy-8-ethyl-5,8-dihydro-pyrido(2,3-d)pyrimidine with 1-allyl-piperazine, as indicated in the preceding Examples. It is a solid which melts in two stages; melting point 131° C., solidification, followed by melting point 143° C. [after recrystallisation from a mixture of benzene (1 volume) and isopropyl ether (1 volume)].

Analysis for $C_{19}H_{25}N_5O_3$ (molecular weight 371.43). Calculated %—C, 61.44; H, 6.78; N, 18.86. Found %—C, 61.10; H, 6.75; N, 18.76.

Saponification of this ester with a 2 N solution of sodium hydroxide in alcohol gives 2-(4'-allyl-piperazino)-5-oxo-8-ethyl-5,8-dihydro-pyrido(2,3-d)pyrimidine-6-carboxylic acid. When recrystallised from a mixture of ethanol (2 volumes) and dimethylformamide (1 volume), it is obtained in a yield of 64%, melting point 203° C.

Analysis for $C_{17}H_{21}N_5O_3$ (molecular weight 343.38). Calculated %—C, 59.46; H, 6.16; N, 20.40. Found %—C, 59.47; H, 5.98; N, 20.38.

EXAMPLE XV 2-(4'-p-Chlorobenzyl-piperazino)-5-oxo-8-ethyl-5,8-dihydro-pyrido(2,3-d)pyrimidine-6-carboxylic acid.

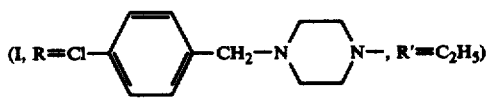

(I, R=Cl—⟨⟩—CH₂—N⟩N—, R'=C₂H₅)

Condensation of 1-p-chlorobenzyl-piperazine with 2-chloro-5-oxo-6-carbethoxy-8-ethyl-5,8-dihydro-pyrido(2,3-d)pyrimidine, as described in Example VII, gives, in a yield of 74%, 2-(4'-p-chlorobenzyl-piperazino)-5-oxo-6-carbethoxy-8-ethyl-5,8-dihydro-pyrido(2,3-d)pyrimidine; melting point 150° C., after recrystallisation from ethyl acetate.

Analysis for $C_{23}H_{26}ClN_5O_3$ (molecular weight 455.5). Calculated %—C, 60.59; H, 5.70; N, 15.36; Cl, 7.79. Found %—C, 60.29; H, 5.72; N, 15.38; Cl, 7.76.

Saponification of this ester gives the corresponding acid; melting point 216° C., when purified by recrystallisation from dimethylformamide (yield 68%).

Analysis for $C_{21}H_{22}ClN_5O_3$ (molecular weight 427.5). Calculated %—C, 58.94; H, 5.14; N, 16.37; Cl, 8.30. Found %—C, 58.88; H, 5.15; N, 16.42; Cl, 8.40.

EXAMPLE XVI 2-(4'-p-Methoxybenzyl-piperazino)-5-oxo-8-ethyl-5,8-dihydro-pyrido(2,3-d)pyrimidine-6-carboxylic acid.

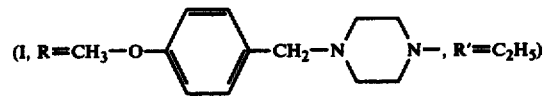

(I, R=CH₃—O—⟨⟩—CH₂—N⟩N—, R'=C₂H₅)

By condensing 2-chloro-5-oxo-6-carbethoxy-8-ethyl5,8-dihydro-pyrido(2,3-d)pyrimidine with 1-p-methoxybenzylpiperazine, following the procedure described in Example VII, 2-(p-methoxybenzyl-piperazino)-5-oxo-6-carbethoxy-8-ethyl-5,8-dihydro-pyrido(2,3-d)pyrimidine is obtained and is purified by recrystallisation from a mixture of isopropyl ether (1 volume) and benzene (1 volume); melting point 136° C.; yield 70%.

Analysis for $C_{24}H_{29}N_5O_4$ (molecular weight 451.51). Calculated % —C, 63.84; H, 6.47; N, 15.51. Found % —C, 63.75; H, 6.41; N, 15.31.

Saponification gives the corresponding acid; melting point 200° C. when purified by recrystallisation from dimethylformamide; yield 60%.

Analysis for $C_{22}H_{25}N_5O_4$ (molecular weight 423.46). Calculated %—C, 62.40; H, 5.95; N, 16.55. Found %—C, 62.42; H, 5.93; N, 16.55.

The anti-microbial activity of the compounds of the invention has been demonstrated in vitro on two different nutrient media:

(a) Trypticase soya medium (T.S.A.), which is very suitable for culturing the majority of microorganisms; it has the following composition:

Trypsin-produced peptone from casein — 15 g
Papain-produced peptone from soya — 5 g
Sodium chloride — 5 g
Agar — 15 g
Water, q.s.p. — 1,000 cm³

After sterilisation, the pH is 7.3.

(b) Ordinarily nutrient agar (N.A.), which is less rich in nutrients, corresponds to the following formulation:

Meat extract — 3 g
Peptone — 5 g
Agar — 15 g
Water, q.s.p. — 1,000 cm³

After sterilisation at 120° C., the pH is 6.8.

Table I gives the minimum inhibitory concentrations (expressed in μg/cm³) for the various microorganisms tested on each medium.

The products were tested on three Gram positive microorganisms (1 to 3) and on 10 Gram negative microorganisms (1 to 3) and on 10 Gram negative microorganisms (4 to 13).

The minimum inhibitory concentrations (M.I.C.) were determined by dilution in the agar media, the ranges of concentration extending from 0.2 to 100 μg/cm³, as a geometric progression with a ratio of 2. Inoculation of the dishes was carried out by means of a multiple inoculator with $10^{-3}$ dilutions of 18 hour broth cultures. The dishes are placed in an oven at 37° C. and readings are made after 18 hours' incubation. The M.I.C. is the lowest concentration which completely inhibits the culture.

The compounds of Examples IV, V, VI, VII, VIII, X and XI to XVI are particularly active against Gram-negative microorganisms, the minimum inhibitory concentration being generally substantially lower in the ordinary medium (N.A.) than in the trypticase-soya medium (T.S.A.).

The compounds of the invention can be used in human or veterinary therapy, especially as antibacterial agents, in pharmaceutical forms which enable them to be administered orally or parenterally. The oral form preferably consists of tablets or gelatine-coated pills each containing 50 to 500 mg of active principle.

For the parenteral forms, it is possible to use aqueous solutions containing 5 to 10% of active product, and having a pH between 6 and 7; isotonicity is achieved by adding sodium chloride if necessary. With compounds which are less soluble in water than the limits fixed above, aqueous solutions of polyethylene glycol (300 or 600) or propylene glycol, at concentrations 10 to 40%, may be used as the solvent. Tertiary amides of lower aliphatic acids such as N-dimethylacetamide and N-diethylacetamide and lactamide, or 5% strength aqueous solutions of benzyl alcohol can also be used as solubilisation adjuvants. The solutions thus produced can be sterilised either by sterile filtration or by autoclaving. They may be dispensed into 5 or 10 $cm^3$ ampoules.

rolidino ring in the 2-position. The minimum inhibitory concentrations were determined five times on each strain by the solid medium (nutrient agar) dilution method. Table III gives the average values found for the three compounds.

It is apparent from this table that the compound of Example VIII is more active on the majority of the Gram negative microorganisms than the 2 other substances.

Furthermore, this product is characterised by a very low toxicity; when administered orally at doses as high as 4 g per kilogram, no deaths were observed amongst the rodents (rats and mice) and a dog was able to undergo a 6 weeks' treatment at 100 mg/kg/day without showing any toxic signs.

When administered orally, the compound of Example VIII is absorbed rapidly and is eliminated principally in the urine. Even with low doses, urinary concentrations are obtained which are very much greater than the minimum inhibitory concentrations effective against the majority of Gram negative microorganisms.

In an experiment involving a 20 kg dog, 50 mg of the

TABLE 1

| Microorganism | Ex. IV T.S.A. | Ex. IV N.A. | Ex. V T.S.A. | Ex. V N.A. | Ex. VI T.S.A. | Ex. VI N.A. | Ex. VII T.S.A. | Ex. VII N.A. | Ex. VIII T.S.A. | Ex. VIII N.A. | Ex. X T.S.A. | Ex. X N.A. | Ex. XI T.S.A. | Ex. XI N.A. |
|---|---|---|---|---|---|---|---|---|---|---|---|---|---|---|
| 1 Staphylococcus 209 P | 50 | 1.6 | 100 | 3.1 | 12.5 | 3.1 | 3.1 | 0.8 | 12.5 | 12.5 | 100 | 50 | >100 | 25 |
| 2 Streptococcus Group A | 12.5 | 12.5 | 6.2 | 25 | 12.5 | 3.1 | 3.1 | 0.8 | 25 | 25 | 100 | 50 | >100 | 25 |
| 3 B. subtilis | 3.1 | 0.8 | 6.2 | 1.6 | 3.1 | 1.6 | 0.8 | 0.4 | 6.2 | 3.1 | >100 | 100 | 100 | 12.5 |
| 4 Bord. bronchiseptica | >100 | 100 | 100 | 50 | >100 | 50 | >100 | 3.1 | 50 | 12.5 | 100 | 25 | 100 | 12.5 |
| 5 B. pyocyaneus A22 | >100 | 100 | 100 | 12.5 | >100 | 50 | >100 | 100 | 12.5 | 25 | >100 | 50 | >100 | 100 |
| 6 B. pyocyaneus TUR | >100 | 100 | 100 | 50 | >100 | 50 | >100 | 100 | >100 | 25 | >100 | 50 | >100 | 100 |
| 7 Esch. Coli 95 | 12.5 | 6.2 | 6.2 | 0.8 | 3.1 | 1.6 | 12.5 | 1.6 | 0.8 | 0.8 | 6.2 | 1.6 | 25 | 1.6 |
| 8 Klebs. pneumoniae | 0.8 | 0.4 | 6.2 | 0.4 | 1.6 | 0.4 | 1.6 | 0.4 | 1.6 | 0.8 | 6.2 | 6.2 | 12.5 | 3.1 |
| 9 Salm. typhi | 12.5 | 6.2 | 3.1 | 3.1 | 6.2 | 12.5 | 12.5 | 1.6 | 1.6 | 6.2 | 12.5 | 3.1 | 50 | 6.2 |
| 10 Sh. sonnei | 12.5 | 3.1 | 1.6 | 0.8 | 1.6 | 1.6 | 12.5 | 1.6 | 0.8 | 0.8 | 3.1 | 12.5 | 12.5 | 1.6 |
| 11 Pr. vulgaris | 12.5 | 3.1 | 6.2 | 1.6 | 6.2 | 50 | 50 | 12.5 | 1.6 | 6.2 | 25 | 3.1 | 50 | 25 |
| 12 Pr. mirabilis | 25 | 12.5 | 6.2 | 6.2 | 12.5 | 3.1 | 100 | 6.2 | 0.8 | 0.8 | 12.5 | 3.1 | 25 | 6.2 |
| 13 Pr. morganii | 0.8 | 0.4 | 1.6 | 0.8 | 1.6 | 1.6 | 12.5 | 3.1 | 0.8 | 0.8 | 6.2 | 3.1 | 25 | 3.1 |

Table (II) gives the minimum inhibitory concentrations of the compounds of Examples XII to XVI, determined on the agar medium, N.A., and expressed in $\mu g/cm^3$.

TABLE II

| Microorganism | Ex. XII | Ex. XIII | Ex. XIV | Ex. XV | Ex. XVI |
|---|---|---|---|---|---|
| 1) Staphylococcus 20 P | 1.6 | 6.2 | 3.1 | 0.8 | 0.4 |
| 2) Streptococcus Group A | 3.1 | 6.2 | 1.6 | 1.6 | 0.8 |
| 3) B. subtilis | 100 | 3.1 | 3.1 | 1.6 | 50 |
| 4) Bord. bronchiseptica | 100 | 12.5 | 3.1 | 3.1 | 12.5 |
| 5) B. pyocyaneus A 22 | 100 | 100 | 25 | 50 | 12.5 |
| 6) Esch. coli 95 | 0.8 | 50 | 50 | 100 | 3.1 |
| 7) Klebs pneumoniae | 0.4 | 1.6 | 0.4 | 0.8 | 0.2 |
| 8) Salm. typhi | 0.8 | 12.5 | 3.1 | 12.5 | 1.6 |
| 9) Sh. sonnei | 0.8 | 1.6 | 0.8 | 1.6 | 0.8 |
| 10) Pr. vulgaris | 0.8 | 6.2 | 3.1 | 12.5 | 6.2 |
| 11) Pr. mirabilis | 6.2 | 12.5 | 6.2 | 12.5 | 12.5 |
| 12) Pr. morganii | 0.8 | 6.2 | 1.6 | 6.2 | 1.6 |

The compound of Example VIII appears to be the most valuable for therapeutic use. It has been tested on 25 bacterial strains, in comparison with nalidixic acid and with the acid of Example III containing a pyrcompound of Example VIII, corresponding to 2.5 mg/kg, were administered by means of a probang. The urine of the animal was removed by catheterisation at the 3rd and at the 7th hour, and the anti-bacterial activity of these samples was measured, taking the compound administered as the reference product. Respective concentrations of 185 $\mu g/cm^3$ (3 hours) and 90 $\mu g/cm^3$ (7 hours) were thus found, the latter concentration being still very much greater than the minimum inhibitory concentrations for the majority of the Gram negative microorganism investigated, especially the Colibacilli and Proteus.

TABLE III

| Microorganism | Nalidixic acid average | standard deviation | Ex. III average | standard deviation | Ex. VIII average | standard deviation |
|---|---|---|---|---|---|---|
| Staphylococcus 209P | 16.24 | 8.4 | 3.42 | 1.68 | 6.22 | 3.5 |
| " 9144 | 25 | 8.84 | 4.04 | 2.06 | 6.22 | 3.5 |
| " SIM | 56.25 | 31.45 | 14.98 | 8.42 | 12.48 | 3.33 |
| Streptococcus A561 | 18.74 | 19.65 | 2.82 | 2.1 | 13.74 | 6.86 |
| " DM19 | 100 | 0 | 100 | 0 | 100 | 0 |
| B. subtilis 6633 | 72 | 0.75 | 1 | 0.6 | 8.1 | 9.54 |
| Bord. bronch. 4617 | 25 | 17.67 | 80 | 27.36 | 75 | 35.35 |
| Ps. aeru- | | | | | | |

TABLE III-continued

| Micro-organism | Nalidixic acid average | standard deviation | Ex. III average | standard deviation | Ex. VIII average | standard deviation |
|---|---|---|---|---|---|---|
| ginosa A$_{22}$ | 60 | 37.91 | 100 | 0 | 12.5 | 0 |
| " 72-345 | 60 | 37.91 | 75 | 35.35 | 13.74 | 6.86 |
| Esch. coli. | | | | | | |
| 95 I.S.M. | 21.87 | 6.25 | 32.5 | 16.77 | 5.14 | 4.57 |
| " 54-127 OMS | 2.15 | 1.14 | 15.625 | 9.5 | 5.66 | 5 |
| " LRB 45 | 3.1 | 2.16 | 15.625 | 9.5 | 2.04 | 1.019 |
| " LRB 67 | 2.7 | 0.75 | 12.5 | 0 | 1.2 | 0.565 |
| " Cho | 4.04 | 2.41 | 32.5 | 16.77 | 2.66 | 2.15 |
| Esch 111 B4 | 2.34 | 1.14 | 15.62 | 9.38 | 1.64 | 1.34 |
| Klebs. pneumoniae 10.031 | 1.4 | 0.4 | 1.2 | 0.33 | 1.88 | 1.039 |
| Salm. typhi 0901 | 2.7 | 0.75 | 23.74 | 16.77 | 2.06 | 2.063 |
| S. enteritidis DANYZ | 2.75 | 2.3 | 21.9 | 18.75 | 1.2 | 0.565 |
| S. oranienburg 10-66 | 100 | 0 | 100 | 0 | 27.5 | 7.5 |
| Arizona 6211 | 3.12 | 1.7 | 27.5 | 13.7 | 1.26 | 1.138 |
| Providencia 0223 | 100 | 0 | 100 | 0 | 16.24 | 8.4 |
| Sh. sonnei I.P.S. | 1.58 | 0.77 | 10.6 | 8.74 | 0.56 | 0.22 |
| Pr. vulgaris 12-53 | 0.88 | 0.438 | 5.6 | 4.08 | 0.36 | 0.09 |
| Pr. mirabilis Nig | 3.42 | 1.68 | 30 | 11.18 | 1.58 | 0.3 |
| Pr. morganii A 236 | 0.36 | 0.26 | 0.56 | 0.22 | 0.4 | 0 |

We claim:

1. Process for the preparation of an 8-alkyl-5-oxo-5,8-dihydro-pyrido(2,3-d)pyrimidine-6-carboxylic acid of the formula:

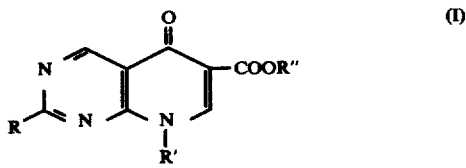

(I)

in which R is hydrogen, lower alkyl, lower alkoxy, lower alkylmercapto, or chloro and R' and R" are lower alkyl, which comprises:

(a) condensing a 4-chloro-5-carbalkoxy-pyrimidine of formula:

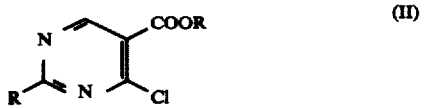

(II)

with a lower alkyl β-amino-propionate of formula:

R' — NH — CH$_2$ — CH$_2$ — COO R"

at about room temperature in a neutral solvent and in the presence of an acceptor of HCl formed during condensation to form a 4-N-(β-carbalkoxyethylamino)-5-carbalkoxy pyrimidine of formula:

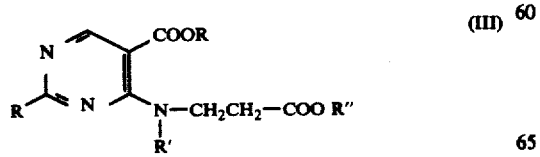

(III)

(b) cyclising the compound of formula III by reaction with an alkaline alcoholate at about room temperature in the presence of an aromatic hydrocarbon to form a 5-oxo-6-carbalkoxy-5,6,7,8-tetrahydro-pyrido(2,3-d)-pyrimidine of formula:

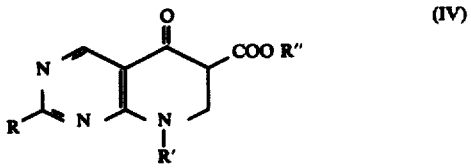

(IV)

(c) halogenating the -keto-ester of formula IV with an agent selected from bromine and sulphurylchloride to yield the corresponding 6-halogeno-derivative, (d) treating the said derivative with a base selected from aliphatic, aromatic to bring about dehydrohalogenation to give a 6-carbalkoxy-5-oxo-5,8-dihydro-pyrido(2,3-d) pyrimidine of formula:

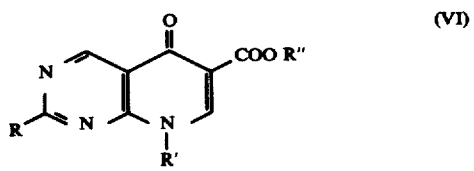

(VI)

2. Process according to claim 1 in which:

(a) a 2-methylmercapto-4-chloro-5-carbethoxy pyrimidine is condensed with a lower alkyl β-amino propionate to form a 2-methyl mercapto-4-N-(β-carbalKoxyethylamino)-5-carbethoxypyrimidine of formula

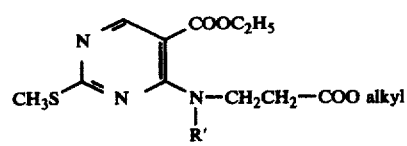

(b) said latter compound is cyclized to form a 2-methyl mercapto-5-oxo-6-carbalkoxy-5,6,7,8-tetra hydro-pyrido (2,3-d) pyrimidine of formula

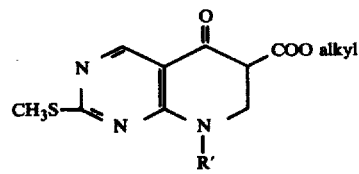

(c) the β-keto ester so obtained is halogenated to yield the corresponding 6-halogeno derivative, (d) the said derivative is treated with a base to bring about dehydrohalogenation to give a 2-methylmercapto-6-carbalkoxy-5-oxo-5,8-dehydro-pyrido (2,3d) pyrimidine of formula

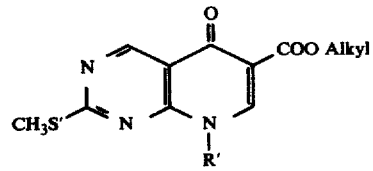

3. Process according to claim 1, in which (a) a 2,4-dichloro-5-carbathoxy pyrimidine is condensed qith a lower alkyl β-amino propionate to form a 2-chloro-4-N-(β-carbalkoxyethylamino)-5-carbithoxypyrimidine of formula

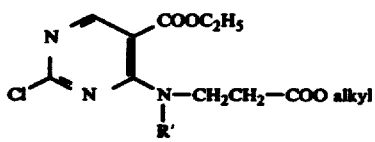

(b) Said latter compound is cyclized to form a 2-chloro-5-oxo-6-carbalkoxy-5,6,7,8-tetrahydro-pyrido(2,3-d)-pyrimidine of formula

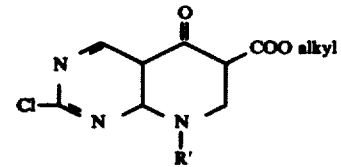

(c) the β-keto ester so obtained is halogenated to yield the compounds 6-halogeno derivative (d) the said derivative is treated with a base to bring about dehydrohalogenation to give a 2-chloro-6-carbalkoxy-5-oxo-5,8-dihydro-pyrido (2,3-d) pyrimidine of formula:

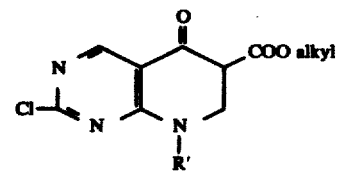

* * * * *